United States Patent [19]

Dopatka

[11] Patent Number: 5,180,664
[45] Date of Patent: Jan. 19, 1993

[54] WASHING SOLUTION, WHICH CONTAINS A COMPLEXING AGENT FOR METAL IONS, FOR A SOLID-PHASE IMMUNOMETRIC METHOD, AND THE USE THEREOF

[75] Inventor: Hans-Detlef Dopatka, Marburg, Fed. Rep. of Germany

[73] Assignee: Behringwerke Aktiengesellschaft, Marburg, Fed. Rep. of Germany

[21] Appl. No.: 798,192

[22] Filed: Nov. 26, 1991

[30] Foreign Application Priority Data

Nov. 28, 1990 [DE] Fed. Rep. of Germany ....... 4037776

[51] Int. Cl.$^5$ .......................................... G01N 33/537
[52] U.S. Cl. .................. 435/7.92; 435/7.91; 435/7.95; 435/28; 436/518; 436/538
[58] Field of Search ...................... 435/7.1, 7.91, 7.92, 435/7.95; 436/518, 538

[56] References Cited

U.S. PATENT DOCUMENTS

| 3,892,841 | 7/1975 | Barg, Jr. | |
|---|---|---|---|
| 4,288,343 | 9/1981 | Louderback | 436/12 |
| 5,017,474 | 5/1991 | McClune et al. | 435/7.92 |
| 5,077,198 | 12/1981 | Shih et al. | 435/7.1 |

FOREIGN PATENT DOCUMENTS

| 0328388A3 | 8/1989 | European Pat. Off. |
| 0337785A1 | 10/1989 | European Pat. Off. |
| 3541978 | 11/1985 | Fed. Rep. of Germany |
| 3541979 | 11/1985 | Fed. Rep. of Germany |
| WO86/04610 | 8/1986 | PCT Int'l Appl. |

OTHER PUBLICATIONS

Use of Experimental Designs With Quantitative ELISA, Burrows, P.M. et al., J. Virol. Meth. 8, 207–216 (1984).
Enzyme Immunoassays In Diagnostic Medicine, Voller A. et al., Bull. World Health Organ. 53, 55–65 (1976).
Solid-Phase Enzyme Immunoassay For Determination Of Antibodies To Cytomegalo-virus, Krishna et al., J. Clin. Microbiol. 12, 46–51 (1980).
Immunoglobulin M To Cytomegalovirus In primary and Reactivation Infections In Renal Transplant Recipients, Chou et al., J. Clin. Microbiol. 25, 52–55 (1987).
Class-Specific Determination Of Antibodies Against Cytomegalo (CMV) and Rubella Virus By ELISA*, Ziegelmaier et al., J. Biol. Standard 9, 23–33 (1981).
Hitachi-Chem. Abst. vol. 99 (1983) p. 172, 393r.

Primary Examiner—Sam Rosen
Attorney, Agent, or Firm—Finnegan, Henderson, Farabow, Garrett and Dunner

[57] ABSTRACT

The invention relates to a washing solution, which contains a complexing agent for metal ions, for solid-phase immunometric assays and to the use of this washing solution.

11 Claims, 3 Drawing Sheets

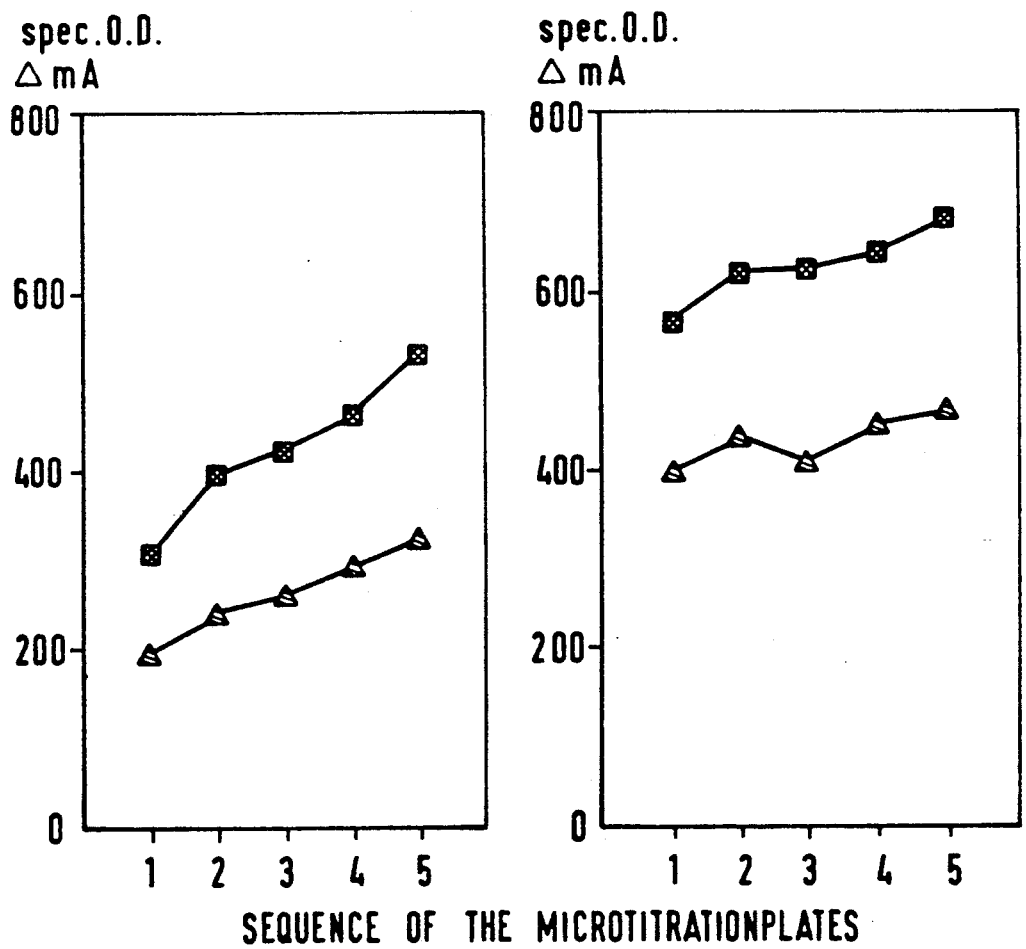
Fig. 1: SEQUENCE AND RESULTS OF ELISA USING INSTRUMENTATION
Fig. 1A — WITHOUT NTA
Fig. 1B — WITH NTA

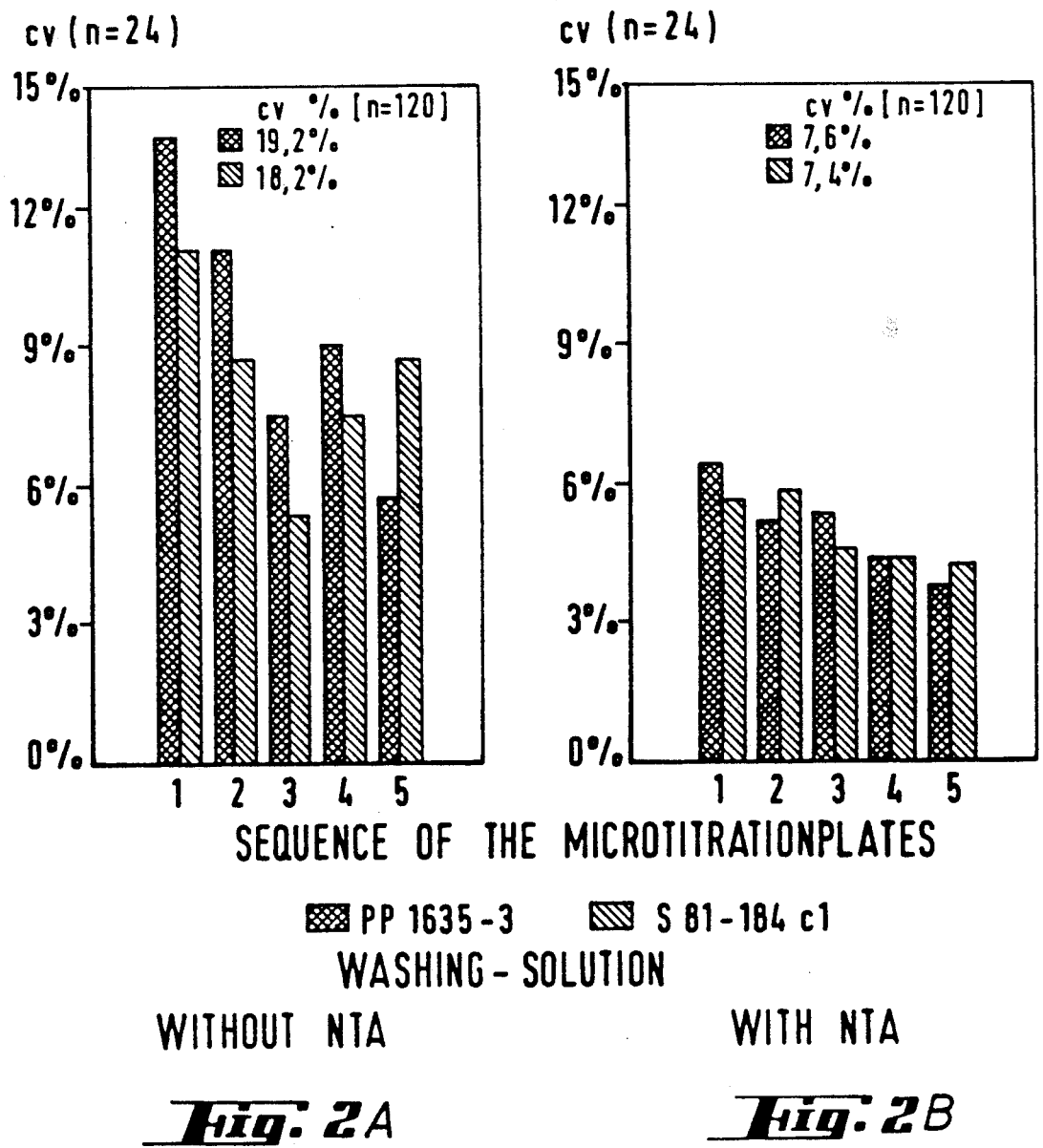

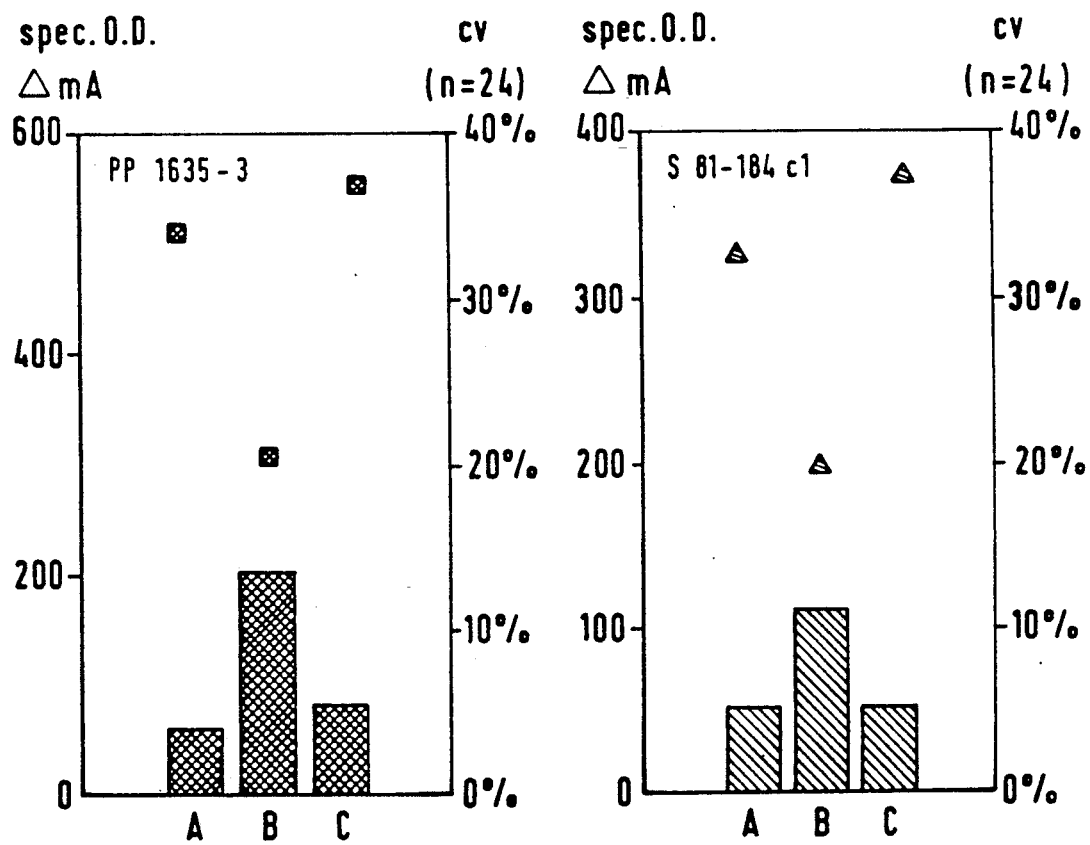
Fig. 3: RESULTS OF ELISA USING DIFFERENT WASHING PROCEDURES
A = MANUAL PROCEDURE WITHOUT NTA
B = AUTOMATIC PROCEDUR WITHOUT NTA
C = AUTOMATIC PROCEDURE WITH NTA

WASHING SOLUTION, WHICH CONTAINS A COMPLEXING AGENT FOR METAL IONS, FOR A SOLID-PHASE IMMUNOMETRIC METHOD, AND THE USE THEREOF

The invention relates to a washing solution, which contains a complexing agent for metal ions, for solid-phase immunometric assays and to the use of this washing solution.

Solid-phase immunometric assays, for example the enzyme-linked immunosorbent assay (ELISA), require one or more washing steps in the procedure. This entails the solid phase being rinsed with the washing solution in order to remove substances which have undergone non-specific attachment, for example immunoglobulins, or excess reagents, for example an enzyme conjugate. If this is carried out in a suitable manner, the result of the assay is a measured signal which corresponds to the concentration of the detected analyte (accuracy). The result of the assay ought in the ideal case to be identical on multiple repetition of the assay for the same analyte concentration (reproducibility). The washing was in the past usually carried out manually using pipettes or washing combs.

It has recently become possible for such solid-phase immunometric assays to be completed by instruments. This entails at least the washing steps being carried out by the instrument.

Instruments in the sense used herein are all instruments with whose aid washing steps in enzyme immunoassays can be carried out mechanically, irrespective of whether these instruments are able to carry out other steps in the completion of ELISA assays.

The known washing solutions, which are composed, for example, of detergent-containing phosphate buffers in the neutral range, have certain disadvantages in these systems. When such instruments are used to complete the washing step, both the accuracy and the reproducibility of the measured signal reach an acceptable level only after some time, i.e. after some plates have been completed (BURROWS, P.M. et al., J. Virol. Meth. 8, 207-216 (1984)).

The present invention was therefore based on the object of finding a possible way of achieving correct results on use of instruments for completing ELISA even on immediate use of these devices. A measured signal which correlates with the concentration of the detected analyte, and the reproducibility of the results obtained, are regarded as criteria for correct assay procedure.

It has now been found, surprisingly, that this object is achieved by the use of a suitable washing solution to which are added, irrespective of the buffer basis, the pH or other additives, complexing agents for metal ions.

The invention therefore relates to a washing solution, which contains a complexing agent for metal ions, for use in heterogeneous enzyme immunoassays.

The invention furthermore relates to the use of a washing solution of this type in a heterogeneous enzyme immunoassay.

The invention also relates to a heterogeneous enzyme immunoassay in which a washing solution which contains a complexing agent for metal ions is used in at least one washing step.

Complexing agents within the meaning of this invention are compounds which are known per se to the person skilled in the art and which preferably enter into complexes with higher-valent metal ions.

Preferred in this connection are complexing agents whose biodegradability is good, such as, for example, nitrilotriacetic acid (NTA), isorin-N,N-diacetic acid (ISDA), gluconic acid and polygluconic acid acetal, and NTA is particularly preferred.

The complexing agent is added in a concentration of 0.01 mmol/l to 100 mmol/l. A concentration of 0.1 to 20 mmol/l is preferred, and a concentration of 1 mmol/l is particularly preferred.

The complexing agent can be added to previously known washing solutions or buffers for solid-phase immunometric assays. One example of these is a 10 mmol/l phosphate buffer composed of $Na_2HPO_4$, $KH_2PO_4$, NaCl (0.45% w/v) and 0.1% (w/v) Tween 20 with a pH of 6.5. This washing solution was mixed according to the invention as example with 1 mmol/l of NTA and used to demonstrate the improvement in the measured signal and the reproducibility achieved therewith in the ELISA.

Heterogeneous enzyme immunoassays are known per se to the person skilled in the art. They can be used to detect antigens and antibodies and can be additive, such as, for example, a sandwich immunoassay, or competitive. The various possible embodiments have been adequately described in the literature. The ELISA method is preferred within the scope of the invention.

Marker enzymes for enzyme immunoassays as such are disclosed in the literature, and alkaline phosphatase, $\beta$-galactosidase and horseradish peroxidase are preferably used, and horseradish peroxidase is particularly preferably used. Solid phases for heterogeneous enzyme immunoassays are known per se to the person skilled in the art, and concave shaped articles such as, for example, tubes or wells, convex shaped articles such as, for example, beads, stars or the like and microparticles (particle size < 1,000 nm) such as, for example, latex particles and magnetically attractable particles are preferably used. Particularly preferred in this context are wells in the form of microtiter plates, latex particles and magnetically attractable particles. Microtiter plates are very particularly preferred.

Materials for solid phases are known to the person skilled in the art. Unless already fixed by the nature of the solid phase, such as, for example, in the case of latex particles, polystyrene is preferably used.

Buffer systems for use in enzyme immunoassays are known to the person skilled in the art. The person skilled in the art is also aware that the nature of the buffer system used in each case depends on the pH to be achieved.

Detergents for use in washing solutions for heterogeneous enzyme immunoassays are likewise known to the person skilled in the art (see, for example, VOLLER, A. et al., Bull. World Health Organ. 53, 55-65 (1976)), and non-ionic and zwitterionic detergents are preferably used; polyoxyethylenes are particularly preferred, and ®Tween 20 is very particularly preferred.

Neutral proteins for use in enzyme immunoassays are known to the person skilled in the art; examples which are preferably used are serum albumins, gelatin, chemically modified gelatin such as, for example, polygeline, and milk proteins such as, for example, lactoferrin, particularly preferred are human or bovine serum albumin, polygeline and lactoferrin, very particularly preferred are polygeline and lactoferrin, the latter prepared as described in German Patent Application 36 38 767.

The person skilled in the art is aware that neutral salts such as, for example, NaCl are added to solutions used in enzyme immunoassays in order to adjust to a defined osmolarity.

Said substances are employed in aqueous solution for use; until used they can be, for example, in lyophilized or granulated form, as dry mixture or in liquid form as final dilution or concentrate.

A preferred embodiment of the washing solution according to the invention has the following composition:

| Buffer | 0–100 mmol/l, preferably 10–20 mmol/l, very preferably 10 mmol/l |
|---|---|
| Detergent | 0–1% (w/v), preferably 0–0.2% (w/v), very preferably 0.1% (w/v) |
| Neutral protein | 0–1% (w/v) |
| Complexing agent | 0.1–20 mmol/l, preferably 1–5 mmol/l, very preferably 1 mmol/l. |

Composition and components of conventional washing solutions are known to the person skilled in the art.

The examples which follow serve to illustrate the invention and in no way represent a restriction.

EXAMPLE 1

An ELISA for detecting IgM against human cytomegalovirus (CMV) was chosen as solid-phase immunometric assay. Polystyrene microtiter plates with 96 reaction wells in an 8×12 field were used as solid phase. CMV cultured in human embryonic fibroblasts, and human embryonic fibroblasts not infected with CMV, were processed by the method of Krishna et al. (1980), J. Clin. Microbiol. 12, 46–51, to preparations which are called hereinafter CMV antigen and (negative) control antigen respectively.

Each microtiter plate was then coated by pipetting 0.1 ml of CMV antigen solution into a reaction well, and 0.1 ml of control antigen solution into an adjacent reaction well, according to the method of the abovementioned authors, in such a way that rows of reaction wells alternately coated for CMV antigen and control antigen were produced. Several assay plates were prepared in the same production cycle in this way.

The prior dilution and the pipetting in of 0.15 ml of the test samples in each case always took place in parallel in adjacent reaction wells which were coated in one case with the CMV antigen and in the other case with the control antigen in accordance with the instructions of Chou et al. (1987), J. Clin. Microbiol. 25, 52–55.

The completion of the ELISA very substantially followed the procedure described by Ziegelmaier et al. (1981), J. Biol. Standard. 9, 23–33, of sample incubation (1), conjugate incubation (2) and substrate incubation (3), with reaction steps (2) and (3) being preceded by a washing step.

ASSARY PROTOCOL

Coating of the solid phase with viral antigen

Washing step*

Step 1: 150 µl **) of test serum in dilution buffer for serum and conjugate (DBSC) are incubated at 37° C. (for IgG and IgM)

Washing step

Step 2: 50 µl of anti-human IgG x AP conjugate in DBSC, 60 min at 37° C.

Washing step

3: 100 µl of p-nitrophenyl phosphate (p-NPP) in substrate buffer, 45 min at 20°–25° C.

Step 4: 50 µl of 2N NaOH

OPTICAL EVALUATION

*) in each case 3×200 µl of washing buffer within 5 min

**) volumes stated in each case per well

These washing steps can be carried out not only manually with a washing comb but also automatically with a device which is connected to a washing solution storage vessel. Examples complying with the state of the art in this connection are the Ultrawasher II from DYNATECH, the Microplate Washer from Flow Laboratories, the Immuno Washer NK 350 from NUNC, the Easy Washer "EAW plus" from SLT LABINSTRUMENTS or the Behring ELISA processor of Behringwerke. The device mentioned last was used in the example which is presented.

The instructions of Ziegelmaier et al. were deviated from by using an anti-human IgM conjugate with peroxidase as marker enzyme, not one with alkaline phosphatase. The substrate chosen for this enzyme was tetramethylbenzidine plus hydrogen peroxide, which had been prepared as described in German Patent Applications 3541978 (Nov. 28, 1985) and 3541979 (Nov. 18, 1985); the development of color has been stopped after 30 min with 0.1 ml of 0.5 N sulfuric acid and measured at 450 nm in a suitable photometer, for example the Titertek ®, Multiskan MC, apparatus from Flow Laboratories or the Behring ELISA processor of Behringwerke. The apparatus mentioned last was used in the example which is presented.

The measured signal obtained with the test sample in the reaction well coated with control antigen was subtracted from the measured signal obtained from the same sample in the reaction well coated with CMV antigen. The difference ($\Delta E$) is called the specific signal (spec. O.D.) and exclusively evaluated.

A simple experimental arrangement was chosen to illustrate the effect of the washing solution on the specificity and reproducibility of the ELISA signal in the case of instrumental completion. An assay plate was coated in multiple replicates (n=24) only with two test samples. One sample was identified as PP 1635-3, and the other as S 81-184cl. Four other assay plates were made up with identical sample charging, and the ELISA was carried out with all five assay plates together.

Care was taken during this that the sequence of the individual assay plates, one to five, remained unchanged in the resulting washing steps.

In the first place, starting from the arithmetic mean of the specific O.D., the signal height on each assay plate was depicted as a function of the washing sequence (FIG. 1A). It was unambiguously evident that the specific O.D. increases with the washing sequence of the assay plates.

Then, starting from the coefficient of variation (CV) of the specific O.D., the signal variation on each assay plate was depicted as a function of the washing sequence FIG. 2A. It was unambiguously evident that the CV becomes lower, i.e. better, with the washing sequence of the assay plates.

If an identical experimental approach is carried out in such a way that NTA, for example 0.1 mmol/l, is added according to the invention to the washing solution, and this washing solution is introduced by a device into the assay, the ELISA result is, surprisingly, found to be considerably more favorable.

The means of the specific O.D. are now, irrespective of the washing sequence of the assay plates, at the signal level corresponding to the concentration of the CMV-specific IgM (FIG. 1B). In addition, the signal variation is, irrespective of the washing sequence of the assay plate, very low (FIG. 2B). If the measurement variation obtained on all five assay plates (overall CV) is evaluated, the improvement, achieved according to the invention, in the reproducibility of the ELISA result is even more distinct. With a washing solution according to the state of the art, the overall CV is 18 to 20% depending on the test sample employed. With a washing solution with the NTA addition according to the invention and the use thereof, the overall CV is 7 to 8% depending on the test sample employed.

EXAMPLE 2

Another experiment is used to compare the known washing methods, with the problems already described, and the washing solution according to the invention and the use thereof for solving the problems. Once again, the same ELISA for detecting IgM against CMV was used to determine the same test samples, namely PP 1635-3 and S 81-184cl, in multiple replicates (n=24). However, this time several different instruments were used to carry out the washing steps. Since the first assay plate completed was particularly greatly affected by the adverse effect, in each case only a single assay plate was washed using the different instruments.

The instruments which were used can be classified in the following way:

A = manual washing using 8-fold multichannel pipette from Flow Laboratories, washing solution without NTA addition according to the invention, B = automatic washing using Behring ELISA processor, washing solution without NTA addition according to the invention, C = automatic washing using Behring ELISA processor, washing solution with NTA addition according to the invention.

The effect of the various instruments in conjunction with a washing solution according to the state of the art and with a washing solution according to the invention on the ELISA result, namely the specific measured signal and its reproducibility, was evaluated.

The arithmetic mean and the coefficient of variation of the specific O.D. were accordingly determined. The result for the abovementioned arrangements A to C is depicted as a graph (FIGS. 3A and 3B).

Combination A is used as control; this is used to show which specific signal corresponds to the concentration of the detected antibody and how reproducible the assay result can be.

It is evident that combination B yields a reduced specific signal and a result of poorer reproducibility.

It is then shown in combination C that this adverse effect is completely eliminated by use of the washing solution according to the invention; the specific signal once again reaches the level corresponding to the concentration of the antibody to be detected, and the reproducibility of the result is thereby ensured.

I claim:

1. A method for the assay of an immunological ligand comprising the steps of:
    a) contacting a specimen suspected on containing said immunological ligand with one or more receptors to said ligand, at least one of which is labeled for detection, to form a detectable immunological complex between said ligand and said one or more receptors,
    b) separating said detectable complex from uncomplexed materials by washing with an aqueous wash solution, which contains a complexing agent for metal ions, and
    c) detecting either the amount of detectable complex or uncomplexed labeled receptor.

2. The method of claim 1, wherein the complexing agent is present in a concentration between 0.01 mmol/1 and 100 mmol/1.

3. The method of claim 1, wherein the complexing agent is biodegradable.

4. The method of claim 1, wherein the complexing agent is NTA.

5. The method of claim 1, wherein the wash solution contains a buffer.

6. The method of claim 1, wherein the wash solution contains a detergent.

7. The method of claim 1 wherein at least one of said receptors is bound to a solid phase.

8. The method of claim 1, wherein the label is an enzyme.

9. The method of claim 1, wherein the washing step is carried out by an apparatus.

10. The method of claim 8, wherein the enzyme is peroxidase.

11. The method of claim 3, wherein the complexing agent is selected from the group consisting of nitrilotriacetic acid (NTA), isorin-N,N-diacetic acid (ISDA), gluconic acid and polygluconic acid acetal.

* * * * *